(12) United States Patent
Alsaifi

(10) Patent No.: US 9,750,895 B1
(45) Date of Patent: Sep. 5, 2017

(54) VENIPUNCTURE

(71) Applicant: Ziad A. Alsaifi, Boise, ID (US)

(72) Inventor: Ziad A. Alsaifi, Boise, ID (US)

( * ) Notice: Subject to any disclaimer, the term of this patent is extended or adjusted under 35 U.S.C. 154(b) by 79 days.

(21) Appl. No.: 14/473,612

(22) Filed: Aug. 29, 2014

(51) Int. Cl.
*A61F 7/00* (2006.01)
*A61M 5/42* (2006.01)
*A61B 5/15* (2006.01)
*A61B 5/153* (2006.01)
*A61B 17/135* (2006.01)
*A61M 25/06* (2006.01)

(52) U.S. Cl.
CPC ............ *A61M 5/427* (2013.01); *A61B 5/1535* (2013.01); *A61B 5/150992* (2013.01); *A61B 17/135* (2013.01); *A61F 7/007* (2013.01); *A61F 2007/0029* (2013.01); *A61M 25/0606* (2013.01)

(58) Field of Classification Search
CPC .............. A61M 5/427; A61M 25/0606; A61B 5/150992; A61B 17/135; A61B 5/1535; A61F 7/007; A61F 2007/0029
See application file for complete search history.

(56) References Cited

U.S. PATENT DOCUMENTS

| | | | | |
|---|---|---|---|---|
| 4,107,509 A | * | 8/1978 | Scher | A61F 7/007 219/527 |
| 4,664,651 A | | 5/1987 | Weinshenker et al. | |
| 4,736,088 A | * | 4/1988 | Bart | A61F 7/007 219/211 |
| 4,747,409 A | * | 5/1988 | Silen | A61F 7/02 607/108 |
| 4,834,802 A | | 5/1989 | Prier | |
| 4,899,749 A | * | 2/1990 | Laroco | A61F 7/08 383/901 |
| 4,920,971 A | * | 5/1990 | Blessinger | A61B 17/135 600/492 |
| 5,312,350 A | | 5/1994 | Jacobs | |
| 5,415,647 A | | 5/1995 | Pisarik | |
| 5,449,379 A | * | 9/1995 | Hadtke | A61B 17/1325 606/203 |
| 5,647,850 A | | 7/1997 | Allen | |
| 6,231,507 B1 | | 5/2001 | Zikorus et al. | |
| 6,464,646 B1 | | 10/2002 | Shalom et al. | |

(Continued)

FOREIGN PATENT DOCUMENTS

WO 9214410 A1 9/1992
WO 2014076479 A1 5/2014

OTHER PUBLICATIONS

Standard Operating Procedure Venepuncture, MRC Bright Study, available at http://www.brightstudy.ac.uk/info/sop08.html, last retrieved on Jun. 6, 2014.

*Primary Examiner* — Julian W Woo
(74) *Attorney, Agent, or Firm* — Jeffrey Parry Intellectual Property Law Group PLLC; Jeffrey C. Parry

(57) ABSTRACT

A venipuncture device may be used for assisting a healthcare provider identify and locate a blood vessel in a patient. According to embodiments, heat is applied to a selected venipuncture site on the patent's limb. A pressure cuff constricts the limb proximal to the venipuncture site, thereby partially occluding blood flow through the blood vessel and engorging the blood vessel and making it more visible to the healthcare provider. The healthcare provider may then carry out various operations on the patient, including but not limited to drawing blood and insertion of an intravenous line.

20 Claims, 5 Drawing Sheets

(56) References Cited

U.S. PATENT DOCUMENTS

| | | | |
|---|---|---|---|
| 6,524,297 B1 | 2/2003 | Newman | |
| 6,565,593 B2 * | 5/2003 | Diana | A61F 7/02 |
| | | | 607/104 |
| 6,652,487 B1 | 11/2003 | Cook | |
| 7,655,023 B2 | 2/2010 | Madison | |
| 7,825,356 B2 * | 11/2010 | Hewes | A61F 7/007 |
| | | | 126/201 |
| 8,721,700 B2 * | 5/2014 | Stuffel | A61F 7/007 |
| | | | 219/211 |
| 2008/0132816 A1 | 6/2008 | Kane et al. | |
| 2009/0177184 A1 | 7/2009 | Christensen et al. | |
| 2011/0172749 A1 | 7/2011 | Christensen et al. | |
| 2013/0331914 A1 | 12/2013 | Lee et al. | |

\* cited by examiner

VENIPUNCTURE

BACKGROUND

Technical Field

The present disclosure relates generally to venipuncture. In particular, the present disclosure relates to methods and devices to assist in identifying and/or locating blood vessels in a patient.

Description of Related Art

Under various circumstances, a healthcare provider may attempt to locate and/or identify a blood vessel of a patient for several various reasons. For example, the healthcare provider may need to find a blood vessel to collect a blood sample from the patient or to insert an intravenous (IV) line into the patient.

Sometimes, finding a suitable blood vessel in a patient poses some difficulty. Some patients may have blood vessels that are not easily visible. Some patients may have fat layers that obscure the blood vessels. Techniques that may be typically carried out to identify a blood vessel include use of an elastic or other type of strip as a tourniquet to temporarily partially block blood flow through the vessel, which may engorge the vessel, thereby aiding the healthcare provider in locating it. Such strips are typically tightened around a patient's limb by manually applying tension to the strip and fastening and/or tying the strip to itself.

SUMMARY

In one embodiment, a venipuncture device is disclosed. The venipuncture device includes a heating element and an inflatable cuff. The cuff is adapted to form a loop around a selected limb of the patient. The cuff operates to partially occlude a blood vessel of the patient while the cuff is inflated. The heating element operates to apply heat to a venipuncture site on the limb distal to the cuff.

In another embodiment, a method of identifying a blood vessel in a patient is disclosed. The method includes positioning a heat source at a selected venipuncture site on a limb of the patient, applying heat to the venipuncture site, wrapping a cuff having an inflatable chamber around the limb proximal to the venipuncture site, inflating the chamber, thereby partially occluding the blood vessel, and removing the heat source from the venipuncture site.

The present disclosure will now be described more fully with reference to the accompanying drawings, which are intended to be read in conjunction with both this summary, the detailed description, and any preferred or particular embodiments specifically discussed or otherwise disclosed. This disclosure may, however, be embodied in many different forms and should not be construed as limited to the embodiments set forth herein; rather, these embodiments are provided by way of illustration only so that this disclosure will be thorough, and fully convey the full scope of the invention to those skilled in the art.

BRIEF DESCRIPTION OF THE DRAWINGS

Non-limiting and non-exhaustive embodiments of the present disclosure are described with reference to the following figures, wherein like reference numerals refer to like parts throughout the various views unless otherwise specified.

Figure 1:
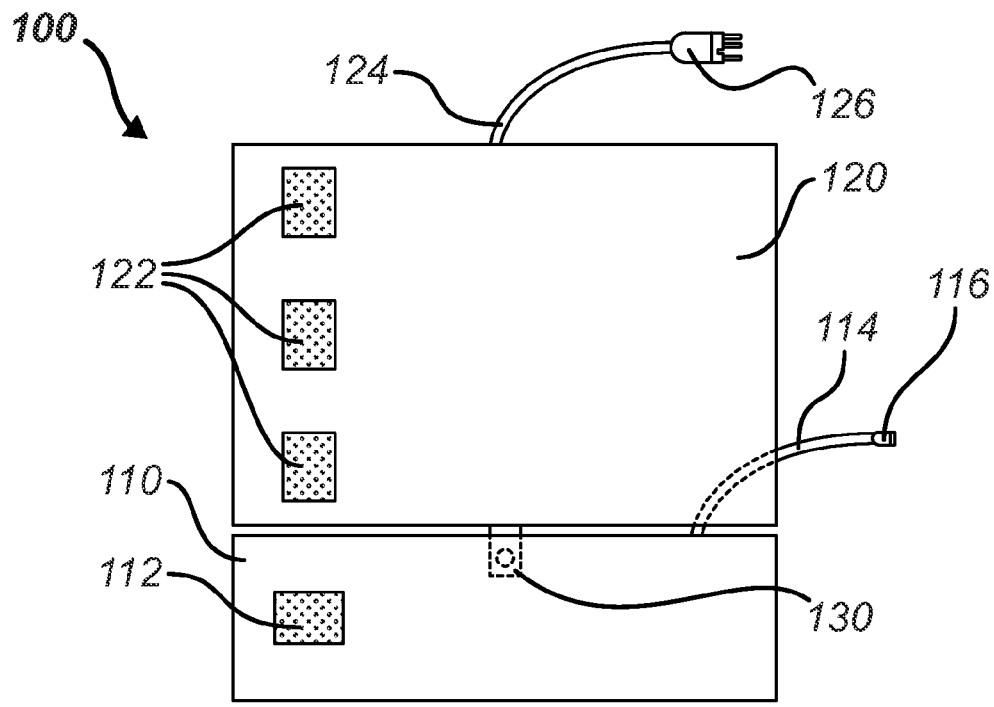
FIG. 1 depicts an embodiment of a venipuncture device according to an embodiment of the present disclosure.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

In the following description, reference is made to exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the spirit and scope of the present disclosure. The following detailed description is, therefore, not to be taken in a limiting sense.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, or characteristics may be combined in any suitable combinations and/or sub-combinations in one or more embodiments or examples.

Embodiments of the present disclosure include methods and devices for facilitating blood vessel engorgement in a patient by applying pressure and heat to a limb of the patient at a venipuncture site. As used herein, the term "patient" includes, but is not limited to, a person or animal that is the subject of medical care, attention, and/or testing. As would be understood by a person of ordinary skill in the art having the benefit of the present disclosure, the patient may be virtually any mammal, including a human, or another type of animal.

Referring to FIG. 1, embodiments of the present disclosure comprise a venipuncture device 100. According to various embodiments, venipuncture device 100 comprises an inflatable cuff 110 and a heat pad 120. In an embodiment, cuff 110 comprises one or more internal chambers and an outer covering. Cuff 110 comprises fasteners 112 adapted to form cuff 110 into a loop around an appendage of the patient. In one embodiment, fasteners 112 comprise hook-and-loop pads adapted to secure to surfaces of cuff 110, thereby forming cuff 110 into a loop. In another embodiment, fasteners 112 comprise adhesive. In alternative embodiments, fasteners 112 comprise other material and/or mechanisms adapted to hold cuff 110 in a loop wrapped around a patient's limb.

In embodiments, cuff 110 has a length proportionate to a patent's limb circumference, such that cuff 110 may wrap around the limb and allow secure fasteners 112 to secure to surface of cuff 110. Various lengths of cuff 110 may be provided so that cuff 110 has an appropriate length to exceed the circumference of a patient's limb, thereby leaving an overlap of cuff material to allow contact between fasteners 112 and surface of cuff 110. For example, cuff 110 may be provided in lengths appropriate for the following categories of human patients: neonatal, pediatric, adult, adult large, and adult thigh. As examples, but not to be taken in a limiting sense, the foregoing categories of human patients may correspond to the following respective lengths of cuff 110: 6-11 cm, 10-19 cm, 18-26 cm, 25-43 cm, and 42-54 cm. According to some sizing systems, cuff 110 may be provided according to standard numerical sizes, for example size 6, 7, 8, 9, 10, 11, 12, or 13. Cuff 110 may be manufactured in other selected lengths as may be dictated by particular patient sizes or other circumstances.

In embodiments, the internal chambers have flexible and/or expandable walls. The internal chambers may be filled with air or other fluid to constrict cuff 110 around a patient's limb to a selected pressure. Air may enter the internal chambers from tube 114 and fill the cuff 110 to a selected pressure. Connector 116 comprises a fitment for attaching tube 114 to a pressurized air source. In embodiments, tube 114 comprises a compliant, flexible material such as thermoplastic polyurethane. In other embodiments, tube 114 is manufactured from other suitable materials.

In embodiments, cuff 110 has a width appropriately large so that while cuff 110 is wrapped around a patient's limb and while the internal chambers are inflated, sufficient pressure may be exerted upon the patient's limb to partially occlude a blood vessel in the patient's limb.

According to various embodiments of the present disclosure, heat pad 120 comprises one or more internal heating elements within a flexible outer covering. Embodiments of heat pad 120 comprise fasteners 122 adapted to form heat pad 120 into a loop around an appendage of the patient. In one embodiment, fasteners 122 comprise hook-and-loop pads adapted to secure to surfaces of heat pad 120, thereby forming heat pad 120 into a loop. In another embodiment, fasteners 122 comprise adhesive. In alternative embodiments, fasteners 122 comprise other material and/or mechanisms adapted to hold heat pad 120 in a loop wrapped around a patient's limb.

In embodiments, heat pad 120 has a length proportionate to a patient's limb circumference to wrap around the limb and secure fasteners 122 together. Various lengths of heat pad 120 may be provided so that heat pad 120 has an appropriate length to exceed the circumference of a patient's limb, thereby leaving an overlap of material to allow contact between fasteners 122 and surface of heat pad 120. According to some embodiments, multiple heat pads 120 of various lengths may be provided according to the circumference of a particular patient's limb. In one embodiment, cuff 110 and heat pad 120 have approximately the same length.

Embodiments of heat pad 120 comprise electrical cord 124 having plug 126 for connection of heat pad 120 to a power source. Embodiments of the present disclosure further comprise a thermo regulator with an automatic shut off function in order to not exceed a selected upper temperature limit. For example, the upper limit may selectively be set at 86 degrees Celsius so as to not cause damage to the skin of a patient.

Cuff 110 and heat pad 120 may be held together by connector tab 130. In an embodiment, connector tab 130 comprises a snap fastener. In alternative embodiments, other types of fasteners and/or adhesives are adapted to hold cuff 110 and heat pad 120 together.

Figure 2:
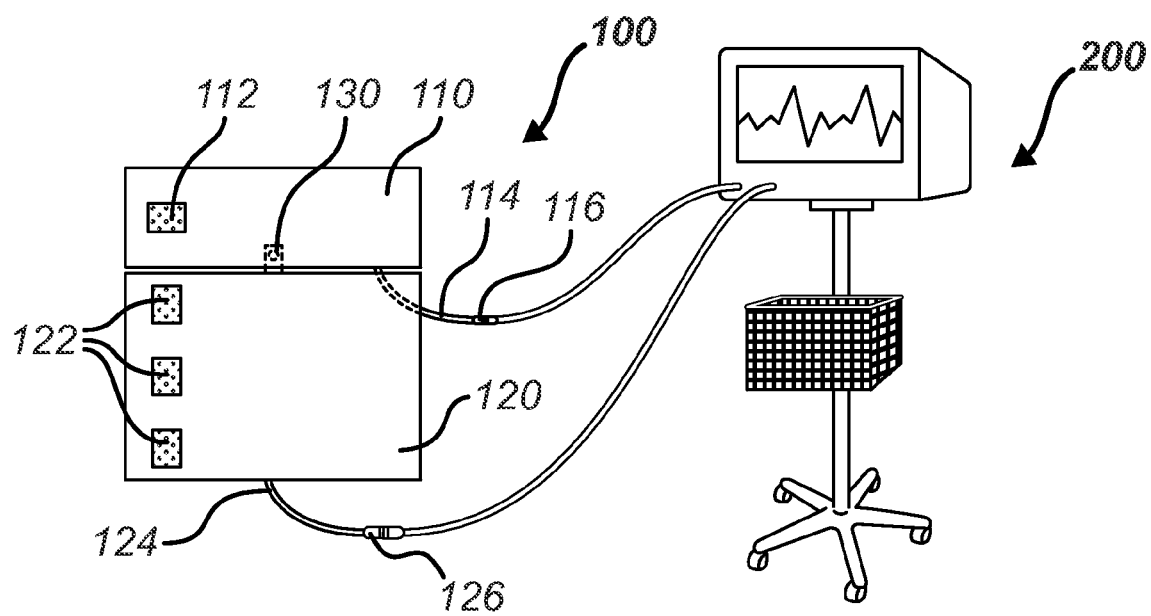
FIG. 2 depicts an embodiment of a venipuncture device and vital signs cart according to an embodiment of the present disclosure.

Referring to FIG. 2, embodiments of venipuncture device 100 may be connected to a vital signs cart 200. In such embodiments, vital signs cart 200 includes a pressurized air source for inflating cuff 110. Embodiments of vital signs cart 200 further include an electrical power source for supplying current to heat pad 120 for heating thereof. In various embodiments, vital signs cart 200 includes a control interface for selecting a pressure to be applied to cuff 110 and/or temperature to be applied to heat pad 120. In some embodiments, vital signs cart 200 includes a memory and/or computer-readable instructions to direct a series of operations including: measuring the patient's blood pressure, determining a target pressure for optimal blood vessel engorgement, activating heat pad 120 to a selected temperature, and inflating cuff 110 to the target pressure.

According to embodiments, vital signs cart 200 may be powered by a wall outlet, a battery, a combination of both, or by other power sources. Vital signs cart may include an onboard air compressor for inflation of cuff 110. Alternatively, an external source may feed pressurized air into cuff 110 via tube 114.

Figure 3A:
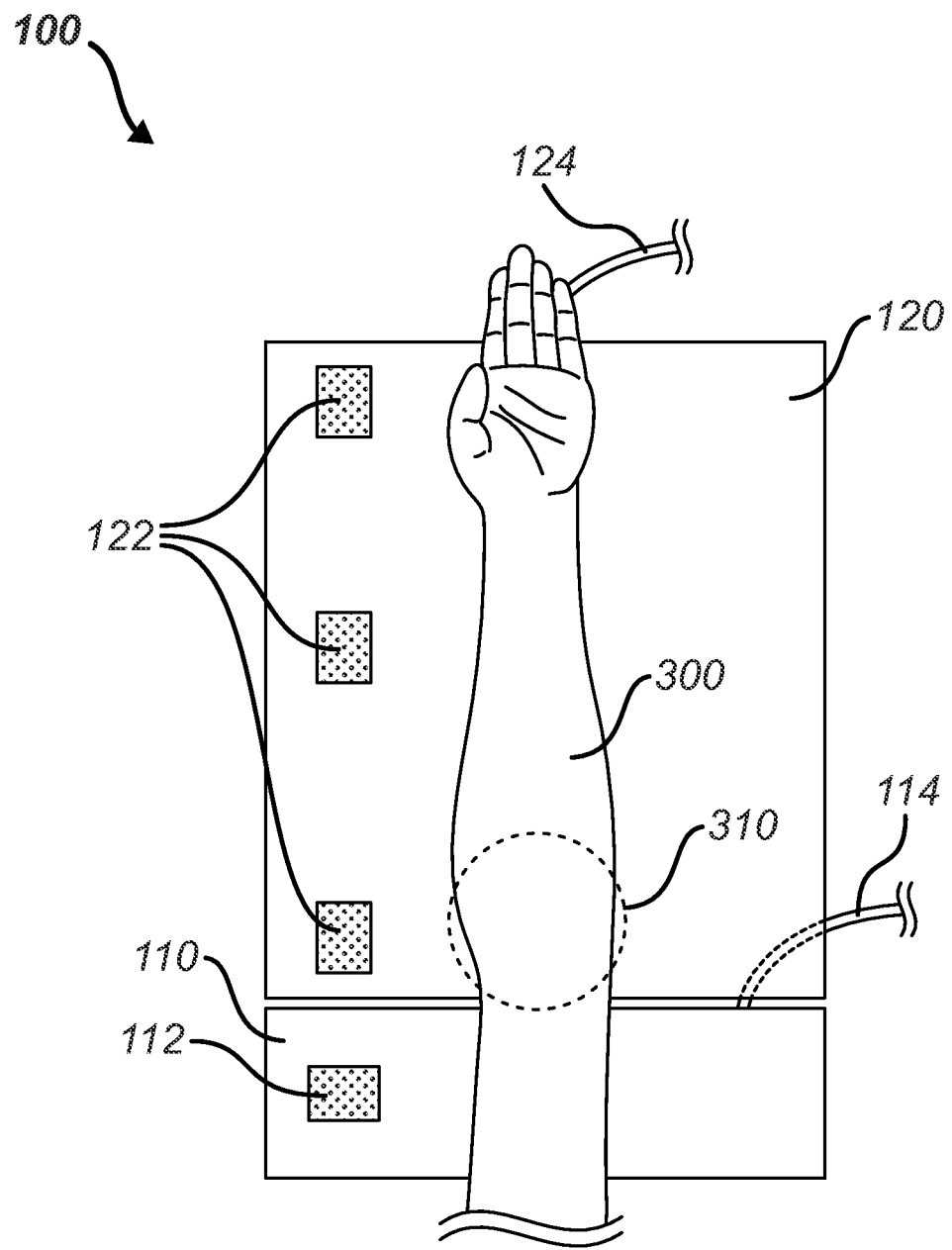
FIGS. 3A-3C depict an application of a venipuncture device according to embodiments of the present disclosure.

In operation, venipuncture device 100 may be used to assist a healthcare provider in identifying and/or locating blood vessels in a patient's extremity. For example, venipuncture device 100 may assist the healthcare provider in locating a blood vessel on the patient's leg and/or arm. Referring to FIG. 3A, a healthcare provider may first place the patient's limb 300 in contact with venipuncture device 100, positioning cuff 110 proximal to a targeted area 310 on the limb. For example, as depicted in FIG. 3A, the selected patient's blood vessel is the patient's median cubital vein. The cuff 110 has been positioned proximal to the venipuncture site 310. In embodiments, the healthcare provider visually examines the venipuncture site 310 to determine if the targeted vein is obvious. If the vein is not sufficiently visible for the healthcare provider to puncture, a decision to use cuff 110, heat pad 120, or both on the patient may be made.

Figure 3B:
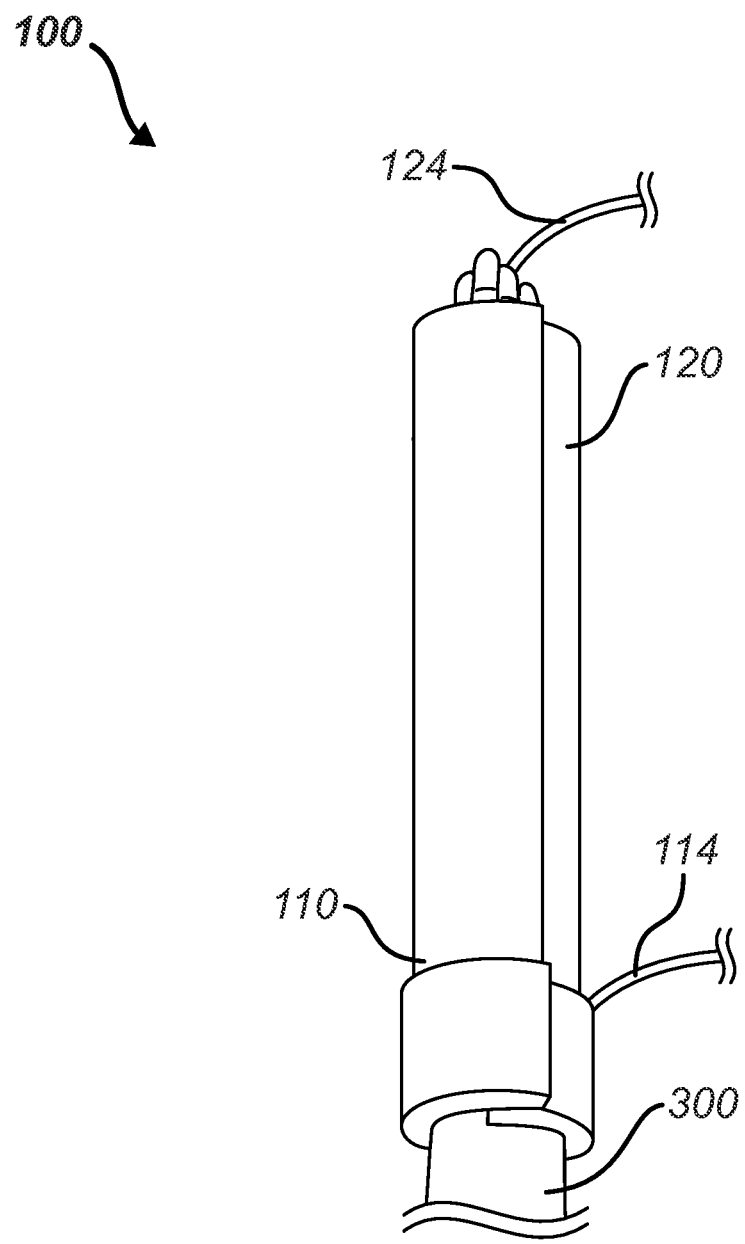

Referring now to FIG. 3B, cuff 110 and heat pad 120 are wrapped around the patient's limb 300 and secured by fasteners 112, 122, forming a snug fit. As depicted, heat pad 120 is wrapped around the venipuncture site 310 and the surrounding area on the patient's limb 300.

In the event of a decision by the healthcare provider that the patient's vein is not sufficiently obvious, heat may be applied to the venipuncture site to engorge the vein. Electrical current may be transmitted along cord 124 thereby powering heat pad 120 to a target temperature and applying heat to the patient's limb 300. In an embodiment, the target temperature of heat pad 120 ranges from 76 degrees Celsius to 82 degrees Celsius. In one embodiment, heat is applied for a period of five to ten minutes to the venipuncture site 310. In other embodiments, the healthcare provider may determine that heat application is not needed. In such circumstances, the heat pad 120 may be separated at tab 130 from pressure cuff 110 and cuff 110 may be wrapped around the patient's limb 300 proximal to the venipuncture site 310 without heat pad 120.

Following placement and wrappage of cuff 110, pressurized air may be passed though tube 114 to inflate cuff 110. According to embodiments, cuff 110 may be inflated to a targeted pressure in order to partially occlude the patient's targeted blood vessel. In one embodiment, the pressure target is the patient's diastolic blood pressure.

In other embodiments, the pressure target is slightly less than the patient's diastolic blood pressure. In embodiments, the pressure target is determined as a percentage of the patient's measured diastolic blood pressure. In one embodiment, the pressure target is 99% of the patient's measured diastolic blood pressure. In another embodiment, the pressure target is 95% of the patient's measured diastolic blood pressure. In another embodiment, the pressure target is 90% of the patient's measured diastolic blood pressure. As an illustrative example, if a patient's blood pressure is measured to be 75 mm Hg, the pressure target can be calculated as 95% of 75 mm Hg, which is 71.3 mm Hg.

In some embodiments, the pressure target is determined as an absolute difference from the patient's measured diastolic blood pressure. In one embodiment, the pressure target is 1 mm Hg less than the patient's measured diastolic blood pressure. In another embodiment, the pressure target is 3 mm Hg less than the patient's measured diastolic blood pressure. In another embodiment, the pressure target is 5 mm Hg less than the patient's measured diastolic blood pressure. As another illustrative example, if a patient's blood pressure is measured to be 75 mm Hg, the pressure target can be calculated as 3 mm Hg less than 75 mm Hg, which is 72 mm Hg.

The patient's diastolic blood pressure may be measured manually by a healthcare provider, for example by using a sphygmomanometer and/or other known methods. Alternatively, the patient's diastolic blood pressure may be measured by using cuff 110 as a sphygmomanometer inflated either by pressured air from vital signs cart 200 or a secondary bulb connected to tube 114. In embodiments, vital signs cart 200 may effectively utilize cuff 110 to operate as an automated sphygmomanometer to measure the patient's diastolic blood pressure.

Figure 3C:
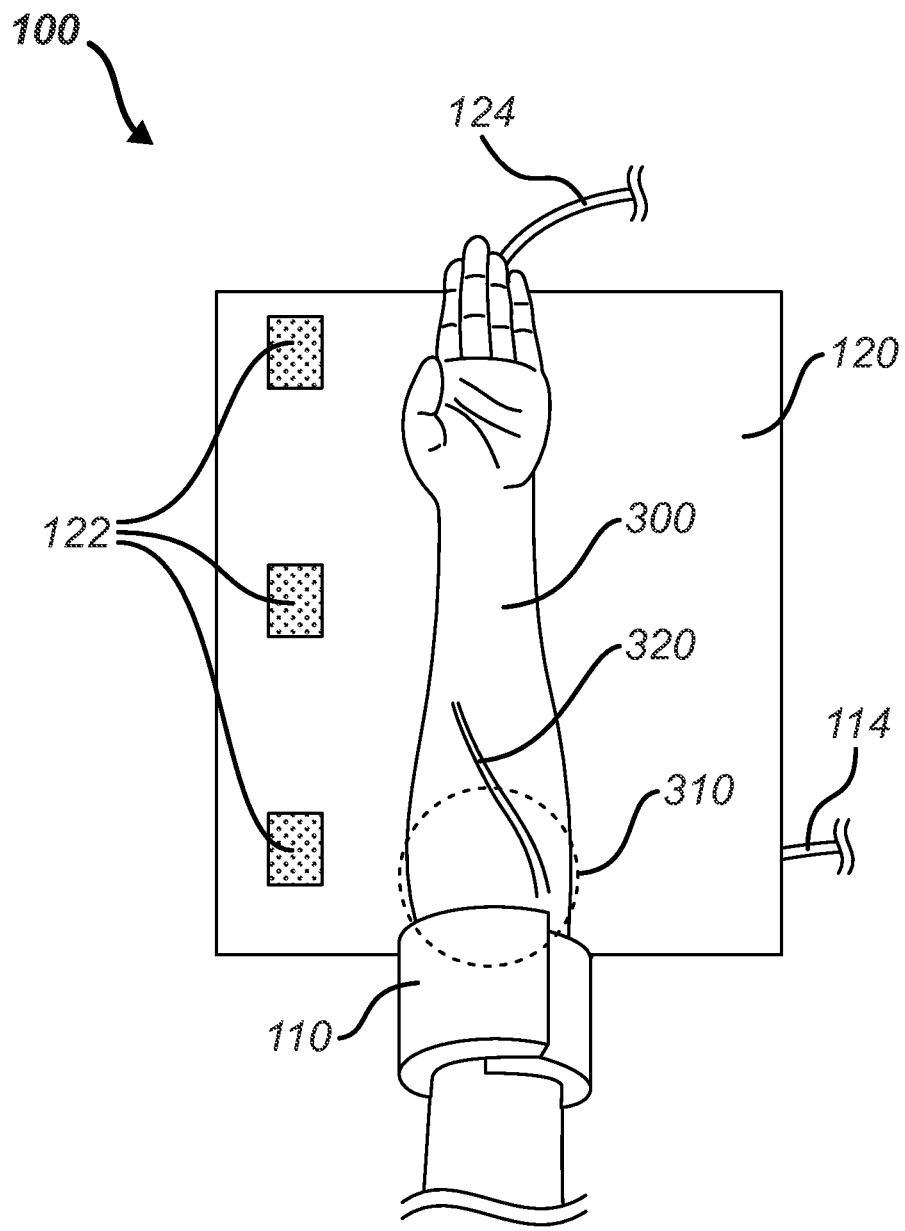

Referring now to FIG. 3C, heat pad 120 may be unwrapped to expose the venipuncture site 310 and give the healthcare provider access thereto. As shown, the patient's median cubital vein 320 is now visibly engorged as a result of the heat and constriction, which may allow the healthcare provider to identify and puncture it with relative ease. The healthcare provider can then draw the patient's blood, pass an intravenous line into the targeted blood vessel, or carry out other desired actions on the patient. Cuff 110 may be left in place at the selected pressure while carrying out such actions, or may be partially or completely deflated.

Figure 4:
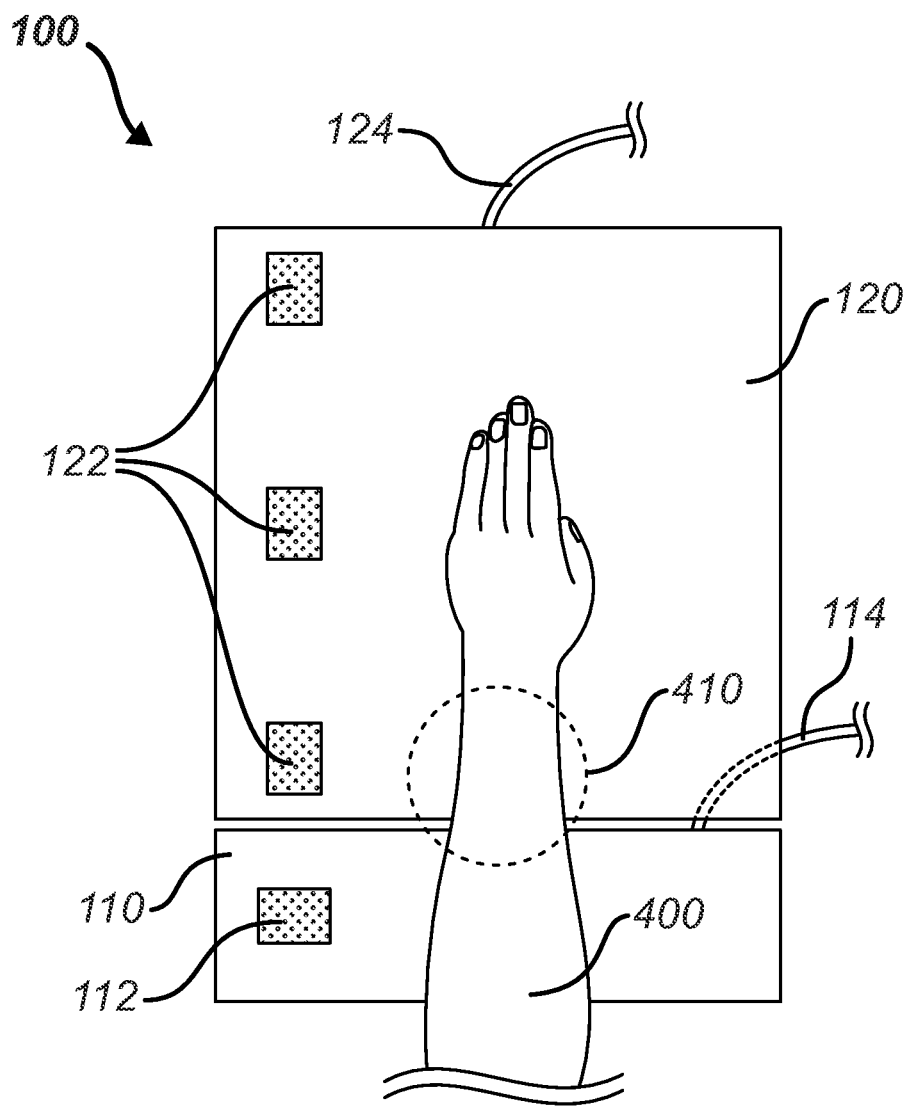
FIG. 4 depicts an application of a venipuncture device to a patient's forearm according to embodiments of the present disclosure.

As stated above, venipuncture device 100 may be applied to various sites on a patient's limb. Referring now to FIG. 4, the patient's basilic vein has been selected as the venipuncture site 410 in an illustrative example. As such, cuff 110 is placed proximal to the venipuncture site 410 and heat pad 120 is placed at and distal to the venipuncture site 410. Heat and/or pressure may then be administered to the venipuncture site to engorge the selected vein similar to the manner described above.

Although the present disclosure is described in terms of certain preferred embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the spirit and scope of the present disclosure.

What is claimed is:

1. A method of venipuncture at a blood vessel in a patient, comprising:
    positioning a heating element of a venipuncture device at a selected venipuncture site on a limb of the patient;
    applying heat to the venipuncture site;
    wrapping a cuff of the venipuncture device around the limb proximal to the venipuncture site, the cuff having an inflatable chamber, wherein:
        the cuff is adapted to form a loop around the limb of the patient and
        the heating element is adapted to apply heat to the venipuncture site on the limb distal to the cuff;
    inflating the chamber, thereby partially occluding the blood vessel;
    removing the heating element from the venipuncture site; and
    inserting an intravenous line into the blood vessel at the venipuncture site.

2. The method of claim 1, further comprising drawing blood from the blood vessel at the venipuncture site.

3. The method of claim 1, wherein applying heat to the venipuncture site comprises applying heat to the venipuncture site for five to ten minutes.

4. The method of claim 1, wherein applying heat to the venipuncture site comprises heating the heat element to a temperature of up to 86 degrees Celsius.

5. The method of claim 4, wherein applying heat to the venipuncture site comprises heating the heat element to 60 to 86 degrees Celsius.

6. The method of claim 1, further comprising selecting a pressure target, wherein inflating the chamber comprises inflating the chamber to the pressure target.

7. The method of claim 6, wherein selecting the pressure target comprises:
    measuring a diastolic blood pressure of the patient and
    setting the pressure target to be equal to or less than the measured diastolic blood pressure.

8. A method of venipuncture at a blood vessel in a patient, comprising:
    positioning a heating element of a venipuncture device at a selected venipuncture site on a limb of the patient;
    applying heat to the venipuncture site;
    wrapping a cuff of the venipuncture device around the limb proximal to the venipuncture site, the cuff having an inflatable chamber, wherein:
        the cuff is adapted to form a loop around the limb of the patient and
        the heating element is adapted to apply heat to the venipuncture site on the limb distal to the cuff;
    inflating the chamber, thereby partially occluding the blood vessel;
    removing the heating element from the venipuncture site; and
    drawing blood from the blood vessel at the venipuncture site.

9. The method of claim 8, further comprising inserting an intravenous line into the blood vessel at the venipuncture site.

10. The method of claim 8, wherein applying heat to the venipuncture site comprises applying heat to the venipuncture site for five to ten minutes.

11. The method of claim 8, wherein applying heat to the venipuncture site comprises heating the heat element to a temperature of up to 86 degrees Celsius.

12. The method of claim 11, wherein applying heat to the venipuncture site comprises heating the heat element to 60 to 86 degrees Celsius.

13. The method of claim 8, further comprising selecting a pressure target, wherein inflating the chamber comprises inflating the chamber to the pressure target.

14. The method of claim 13, wherein selecting the pressure target comprises:
measuring a diastolic blood pressure of the patient and
setting the pressure target to be equal to or less than the measured diastolic blood pressure.

15. A method of venipuncture at a blood vessel in a patient, comprising:
positioning a heating element of a venipuncture device at a selected venipuncture site on a limb of the patient;
applying heat to the venipuncture site;
wrapping a cuff of the venipuncture device around the limb proximal to the venipuncture site, the cuff having an inflatable chamber, wherein:
the cuff is adapted to form a loop around the limb of the patient and
the heating element is adapted to apply heat to the venipuncture site on the limb distal to the cuff;
selecting a pressure target by:
measuring a diastolic blood pressure of the patient and
setting the pressure target to be equal to or less than the measured diastolic blood pressure;
inflating the chamber to the pressure target, thereby partially occluding the blood vessel; and
removing the heating element from the venipuncture site.

16. The method of claim 15, further comprising inserting an intravenous line into the blood vessel at the venipuncture site.

17. The method of claim 15, further comprising drawing blood from the blood vessel at the venipuncture site.

18. The method of claim 15, wherein applying heat to the venipuncture site comprises applying heat to the venipuncture site for five to ten minutes.

19. The method of claim 15, wherein applying heat to the venipuncture site comprises heating the heat element to a temperature of up to 86 degrees Celsius.

20. The method of claim 19, wherein applying heat to the venipuncture site comprises heating the heat element to 60 to 86 degrees Celsius.

\* \* \* \* \*

UNITED STATES PATENT AND TRADEMARK OFFICE
CERTIFICATE OF CORRECTION

PATENT NO. : 9,750,895 B1  
APPLICATION NO. : 14/473612  
DATED : September 5, 2017  
INVENTOR(S) : Ziad A. Alsaifi Page 1 of 1

It is certified that error appears in the above-identified patent and that said Letters Patent is hereby corrected as shown below:

On the Title Page

In the abstract, Line 4, the word "patent's" should be changed to --patient's--.

In the Specification

Column 3, Lines 6 and 52, the words "patent's", each occurrence, should read --patient's--.

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*